US00PP15305P2

(12) United States Plant Patent
Fischer-Toehl

(10) Patent No.: US PP15,305 P2
(45) Date of Patent: Nov. 9, 2004

(54) ***GERANIUM* PLANT NAMED 'BALSHOPINK'**

(50) Latin Name: *Pelargonium×hortorum*
Varietal Denomination: Balshopink

(75) Inventor: Ilse Fischer-Toehl, Kirchlinteln (DE)

(73) Assignee: Silze GmbH & Co. JG, Weener (DE)

( * ) Notice: Subject to any disclaimer, the term of this patent is extended or adjusted under 35 U.S.C. 154(b) by 0 days.

(21) Appl. No.: 10/726,340

(22) Filed: Dec. 3, 2003

(51) Int. Cl.[7] ..... A01H 5/00
(52) U.S. Cl. ..... Plt./329
(58) Field of Search ..... Plt./329, 328

*Primary Examiner*—Kent Bell
(74) *Attorney, Agent, or Firm*—Wood, Phillips, Katz, Clark & Mortimer

(57) ABSTRACT

A new and distinct cultivar of *geranium* plant named 'Balshopink', characterized by its semi-double pink-colored flowers, dark green-colored foliage with faint zone, and vigorous upright and mounded growth habit.

2 Drawing Sheets

Latin name of genus and species of plant claimed: *Pelargonium×hortorum.*
Variety denomination: 'Balshopink'.

BACKGROUND OF THE INVENTION

The present invention relates to a new and distinct cultivar of *geranium* plant botanically known as *Pelargonium× hortorum* and hereinafter referred to by the cultivar name 'Balshopink'.

The new cultivar originated in a controller breeding program in Weener, Germany during the summer of 1997. The purpose of the breeding program was the creation of *geranium* plants with vigorous upright mounded growth habits, dark green foliage, and unique flower colors.

The female parent of 'Balshopink' was 'Sel Lady' (not patented). The male parent of 'Balshopink' was 'Sel Kitty' (not patented). The new *geranium* was discovered and selected by the inventor as a single flowering plant within the progeny of the above stated cross-pollination during the summer of 1998 at Weener, Germany and was initially designated 'E-105'.

Asexual reproduction of the new cultivar by terminal stem cuttings taken since 1998 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length, without, however, any variance in genotype.

It was repeatedly found that the cultivar of the present invention:

1. Forms semi-double pink-colored flowers.
2. Forms dark green-colored leaves with faint zonation, and
3. Exhibits a vigorous upright and mounded growth habit.

Plants of the new cultivar differ from plants of the parent cultivars primarily in flower color and growth habit.

Of the many commercially available *geranium* cultivars known to the inventor, the most similar in comparison to 'Balshopink' is 'BSR-284 Pink' (U.S. Plant Pat. No. 8,287). However, in side-by-side comparisons, plants of 'Balshopink' differ from plants of 'BSR-284 Pink' in the following characteristics:

1. Plants of 'Balshopink' exhibit smaller flowers than plants of 'BSR-284 Pink', and
2. Plants of 'Balsopink' have longer peduncles than plants of 'BSR-284 Pink'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from color values cited in the detailed description, which accurately describes the colors of 'Balshopink'. The plants were grown for 8 weeks in a greenhouse at West Chicago, Ill.

DETAILED BOTANICAL DESCRIPTION

Figure 1:
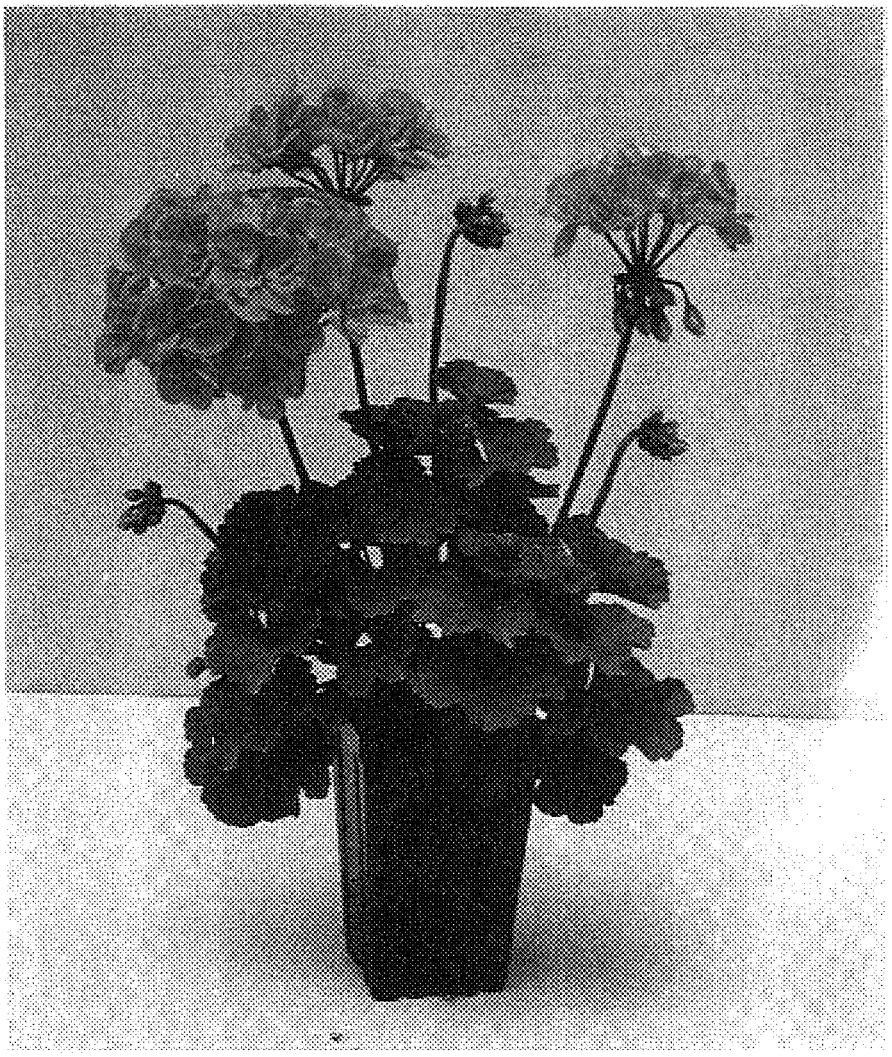
FIG. 1 illustrates an overall view of the growth and flowering habit of 'Balshopink'.
Figure 2:
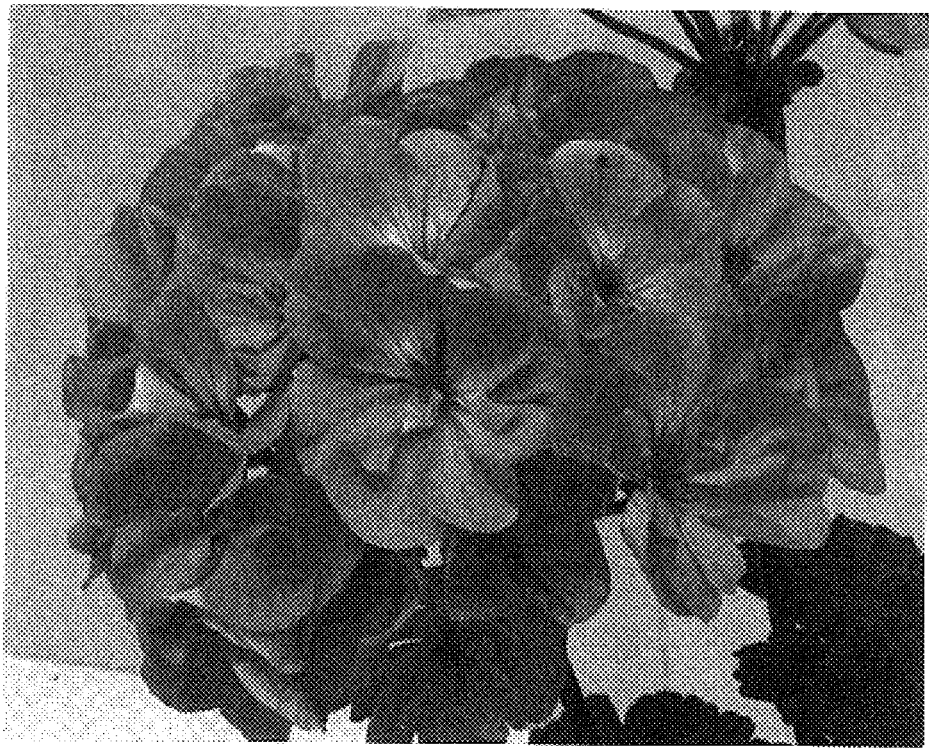
FIG. 2 illustrates a close-up view of a single umbel of 'Balshopink'.
Figure 3:
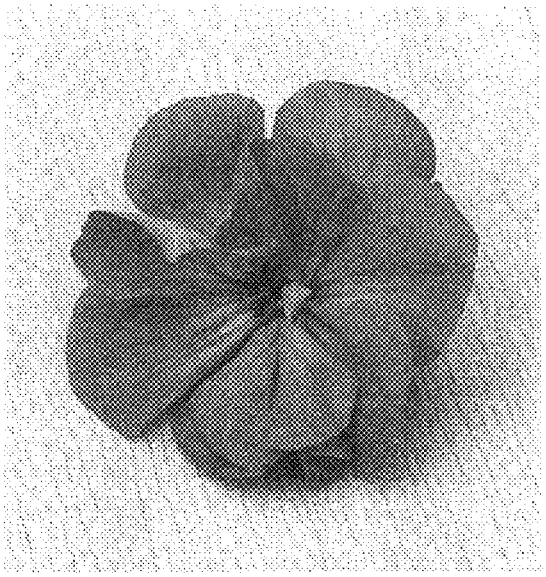
FIG. 3 illustrates a close-up view of a single flower of 'Balshopink'.

The chart used in the identification of colors described herein is The R.H.S. Colour Chart of The Royal Horticultural Society, London, England, 1995 edition, except where general color terms of ordinary significance are used. The color values were determined on Jun. 20, 2003 in West Chicago, Ill. The readings were taken between 10:00 and 11:45 a.m. under natural day light conditions.

The plants used for the following measurements and descriptions were produced from cuttings taken from stock plants and grown in a double polycarbonate covered greenhouse in West Chicago, Ill. under conditions comparable to those used in commercial practice. The plants were grown in 10 cm pots for 8 weeks utilizing a soilless growth medium. Greenhouse temperatures were maintained at approximately 65°–70° F. (18°–21° C.) during the day and approximately 60°–65° F. (15°–18° C.) during the night. Greenhouse light levels of 4,000 to 6,000 footcandles were maintained during the day. Plants were pinched at three weeks after planting.

Botanical classification: *Pelargonium×hortorum* cultivar 'Balshopink'.

Parentage:

*Female parent.*—*Pelargonium×hortorum* cultivar 'Sel Lady' (not patented).

*Male parent.*—*Pelargonium×hortorum* cultivar 'Sel Kitty' (not patented).

Propagation:

*Type cutting.*—Terminal stem.

*Time to initiate roots.*—Approximately 10 to 14 days.

*Time to develop roots.*—Approximately 21 to 28 days.

*Root description.*—Fibrous.

*Rooting habit.*—Well branched.

Plant description:

*Growth habit and general appearance.*—Vigorous, upright and mounded.

*Height.*—From soil level to top of foliage: Approximately 12.7 cm. From soil level to top of plant plane: Approximately 21.5 cm.

*Width/area of spread.*—Approximately 23.6 cm.

*Branching habit.*—Freely basal branching. Approximately 3 branches per plant. Pinching 14 to 21 days after transplanting helps to improve basal branching.

*Branch description.*—Length: Approximately 5.5 cm. Diameter: Approximately 6 mm. Color: 144B with faint overlay of 187A except at nodes. Texture: Hirsute. Internode length at center of branch: Approximately 1.6 cm.

*Foliage description.*—Form: Simple. Arrangement: Opposite. Number of leaves per lateral branch: Approximately 9. Shape: Reniform. Margin: Crenate. Apex: Rounded. Base: Cordate. Venation pattern: Palmate. Upper surface texture: Moderately pubescent. Lower surface texture: Moderately pubescent with dense pubescence along veins. Color of mature foliage: Upper surface: 147A with veins of 144B and faint zone of slightly darker than 147A. Lower surface: 147B with veins of 144B. Size: Mature leaf length: Approximately 4.7 cm. Mature leaf width: Approximately 7.8 cm. Petiole length: Approximately 5.3 cm. Petiole diameter: Approximately 2.5 mm. Petiole Texture: Pubescent on both upper and lower surface. Petiole color: 144A.

Flower description:

*Outdoor flowering habit.*—'Balshopink' is freely flowering under outdoor growing conditions with substantially continuous blooming from spring through fall.

*Time of first flower.*—Approximately 8 weeks after planting of rooted cutting.

*Lastingness of individual bloom.*—Approximately 5–7 days.

Inflorescence description:

*Type.*—Hemispherical umbel. Position: Above foliage. Number of open umbels at any one time: Approximately 2. Number of developing umbels at any one time: Approximately 2. Umbel diameter: Approximately 12.9 cm. Umbel height/depth: Approximately 6.4 cm. Number of flowers per umbel: Approximately 35.

*Peduncle.*—Strong, erect. Length: Approximately 12.4 cm. Diameter: Approximately 4 mm. Texture: Puberulent. Color: 144B with overlay of 187A.

Flower description:

*Bud just before opening.*—Shape: Elliptic. Length: Approximately 1.5 cm. Diameter: Approximately 7.8 mm. Petal color: 62B. Sepal color: 144A with overlay of 187B.

*Corolla.*—Form: Semi-double. Shape: Round, slightly cupped. Diameter/Width: Approximately 5 cm. Depth: Approximately 1.7 cm. Fragrance: None. Persistent.

*Petals/petaloids.*—Quantity: Approximately 7 petals and 2 petaloids per flower. Arrangement: Imbricate. Shape: Obovate. Apex: Obtuse. Base: Attenuate. Margin: Entire. Texture of upper and lower surface: Smooth. Upper petal length: Approximately 2.6 cm. Upper petal width: Approximately 2 cm. Lower petal length: Approximately 2.4 cm. Lower petal width: Approximately 2.1 cm. Color of all petals: Fully opened, upper surface: N66C. Upper petals have 'eye' of 73D at base. Fully opened, lower surface: N66D with veins of N66B.

*Pedicel.*—Strength: Strong. Angle: Erect. Length: Approximately 4 cm. Diameter: Approximately 1 mm. Texture: Soft, short dense hairs. Color: 144B with dense overlay of 185B.

*Sepals.*—Quantity per flower: 5. Shape: Elliptic. Apex: Acuminate. Base: Truncate. Margin: Entire. Length of largest sepal: 1.4 cm. Width of largest sepal: 5 mm. Length of smallest sepal: 1.4 cm. Width of smallest sepal: 2 mm. Texture: Upper surface (inside): Glabrous. Lower surface (outside): Puberulent. Color of all sepals: Upper and lower surface: 144A with overlay of 187B.

*Reproductive organs.*—Androecium: Stamen number: 5 per flower. Filament quantity: Approximately 10. Filament color: N155B. Anther quantity: Approximately 9. Anther length: Approximately 2 mm. Immature after color: 52B. Mature anther color: 61B. Pollen amount: Abundant. Pollen color N30C. Gynoecium: Pistil quantity: One per flower. Pistil length: Approximately 9 mm. Stigma shape: 5 pointed star. Stigma length: 2 mm. Stigma color: 58B. Style length: 2 mm. Style color: 58A. Ovary length: 5 mm. Ovary diameter: 2 mm. Ovary texture: Sericeous. Ovary color: 143C at base; 178A at tip.

Seed and fruit production: Neither seed nor fruit production has been observed.

Disease and pest resistance: Resistance to pathogens and pests common to *geraniums* has not been observed.

Hardiness zone: 'Balshopink' is hardy in zones nine (9) and above.

What is claimed is:

1. A new and distinct cultivar of *geranium* plant named 'Balshopink' substantially, as herein shown and described, which:

1. Forms semi-double pink-colored flowers,
2. Forms dark green-colored foliage with a faint zone, and
3. Exhibits a vigorous upright and mounded growth habit.

* * * * *